United States Patent
Higgins

(10) Patent No.: US 9,936,970 B2
(45) Date of Patent: Apr. 10, 2018

(54) DEVICES, SYSTEMS AND METHODS FOR AN OSCILLATING CROWN DRIVE FOR ROTATIONAL ATHERECTOMY

(71) Applicant: Cardiovascular Systems, Inc., St. Paul, MN (US)

(72) Inventor: Joseph Peter Higgins, Minnetonka, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 656 days.

(21) Appl. No.: 14/454,399

(22) Filed: Aug. 7, 2014

(65) Prior Publication Data

US 2014/0350582 A1    Nov. 27, 2014

Related U.S. Application Data

(63) Continuation-in-part of application No. 14/208,585, filed on Mar. 13, 2014, now Pat. No. 9,750,525.

(60) Provisional application No. 61/782,184, filed on Mar. 14, 2013.

(51) Int. Cl.
   *A61B 17/3207*   (2006.01)
   *A61B 17/00*     (2006.01)
   *A61B 17/22*     (2006.01)

(52) U.S. Cl.
   CPC ............ *A61B 17/320758* (2013.01); *A61B 2017/00154* (2013.01); *A61B 2017/00172* (2013.01); *A61B 2017/00553* (2013.01); *A61B 2017/22014* (2013.01); *A61B 2017/320766* (2013.01)

(58) Field of Classification Search
   CPC ........... A61B 17/320758; A61B 2017/320766; A61B 2017/320775; A61B 2017/22015; A61B 17/2202; A61B 2017/22021; A61B 17/3207; A61B 17/320733; A61B 17/32002; A61B 2017/320032
   USPC ........... 606/108, 159, 167, 170, 180; 604/22
   See application file for complete search history.

(56) References Cited

U.S. PATENT DOCUMENTS

| | | |
|---|---|---|
| 4,445,509 A | 5/1984 | Auth |
| 4,990,134 A | 2/1991 | Auth |
| 5,026,384 A | 6/1991 | Farr et al. |
| 5,030,201 A | 7/1991 | Palestrant |
| 5,041,082 A | 8/1991 | Shiber |
| 5,078,723 A | 1/1992 | Dance et al. |

(Continued)

OTHER PUBLICATIONS

International Preliminary Report on Patentability for PCT Application No. PCT/US2015/041300, filed Jul. 21, 2015, dated Feb. 16, 2017.

*Primary Examiner* — Eric Rosen
*Assistant Examiner* — Chima Igboko
(74) *Attorney, Agent, or Firm* — Barnes & Thornburg LLP; Jeffrey R. Stone

(57) ABSTRACT

The present invention is directed in various methods, devices and systems relating to rotational atherectomy. More specifically, an oscillating driver is connected to a drive shaft, or torque transfer tube, with abrasive element mounted thereon. The result provides a rotational working diameter for the rotating abrasive element that is larger than its resting diameter. Generally, the preferred abrasive element is concentric in profile and/or with center of mass collinear with the drive shaft's rotational axis. However, eccentric abrasive elements, both in terms of offsetting center of mass and/or geometric eccentricity may also be employed.

19 Claims, 4 Drawing Sheets

(56) References Cited

U.S. PATENT DOCUMENTS

| | | | |
|---|---|---|---|
| 5,087,265 A | 2/1992 | Summers | |
| 5,100,425 A | 3/1992 | Fischell et al. | |
| 5,116,352 A | 5/1992 | Schnepp-Pesch et al. | |
| 5,158,564 A | 10/1992 | Schnepp-Pesch et al. | |
| 5,217,474 A | 6/1993 | Zacca et al. | |
| 5,242,460 A | 9/1993 | Klein et al. | |
| 5,308,354 A | 5/1994 | Zacca et al. | |
| 5,312,427 A | 5/1994 | Shturman | |
| 5,314,438 A | 5/1994 | Shturman | |
| 5,360,432 A | 11/1994 | Shturman | |
| 5,370,651 A | 12/1994 | Summers | |
| 5,431,673 A | 7/1995 | Summers et al. | |
| 5,490,859 A | 2/1996 | Mische et al. | |
| 5,501,694 A | 3/1996 | Ressemann et al. | |
| 5,540,707 A | 7/1996 | Ressemann et al. | |
| 5,554,163 A | 9/1996 | Shturman | |
| 5,584,843 A | 12/1996 | Wulfman et al. | |
| 5,662,603 A | 9/1997 | Gelbfish | |
| 5,792,157 A | 8/1998 | Mische et al. | |
| 5,836,868 A | 11/1998 | Ressemann et al. | |
| 5,843,103 A | 12/1998 | Wulfman | |
| 6,096,054 A * | 8/2000 | Wyzgala | A61B 17/320725 606/170 |
| 6,146,395 A | 11/2000 | Kanz et al. | |
| 6,416,523 B1 | 7/2002 | Lafontaine | |
| 6,428,551 B1 | 8/2002 | Hall et al. | |
| 6,494,890 B1 | 12/2002 | Shturman et al. | |
| 6,497,711 B1 | 12/2002 | Plaia et al. | |
| 6,554,846 B2 | 4/2003 | Hamilton et al. | |
| 6,596,005 B1 | 7/2003 | Kanz et al. | |
| 6,758,851 B2 | 7/2004 | Shiber | |
| 7,037,316 B2 | 5/2006 | McGuckin, Jr. et al. | |
| 7,507,245 B2 | 3/2009 | Shturman et al. | |
| 8,137,370 B2 | 3/2012 | Deng | |
| 8,177,801 B2 | 5/2012 | Kallok et al. | |
| 8,337,516 B2 | 12/2012 | Escudero et al. | |
| 8,348,965 B2 | 1/2013 | Prudnikov et al. | |
| 8,353,923 B2 | 1/2013 | Shturman | |
| 8,551,128 B2 | 10/2013 | Hanson et al. | |
| 8,597,313 B2 | 12/2013 | Thatcher et al. | |
| 8,628,551 B2 | 1/2014 | Hanson et al. | |
| 2001/0004700 A1 | 6/2001 | Honeycutt et al. | |
| 2003/0040763 A1* | 2/2003 | Moutafis | A61B 17/320758 606/167 |
| 2003/0199889 A1 | 10/2003 | Kanz et al. | |
| 2004/0147934 A1* | 7/2004 | Kiester | A61B 17/32002 606/80 |
| 2005/0149084 A1 | 7/2005 | Kanz et al. | |
| 2008/0161840 A1 | 7/2008 | Osiroff et al. | |
| 2008/0306498 A1 | 12/2008 | Thatcher et al. | |
| 2009/0069829 A1 | 3/2009 | Shturman | |
| 2009/0105736 A1 | 4/2009 | Prudnikov et al. | |
| 2009/0149877 A1 | 6/2009 | Hanson et al. | |
| 2009/0264908 A1* | 10/2009 | Kallok | A61B 17/320758 606/159 |
| 2009/0299392 A1 | 12/2009 | Rivers | |
| 2009/0306691 A1 | 12/2009 | Cambronne et al. | |
| 2010/0010492 A1 | 1/2010 | Lockard et al. | |
| 2011/0213391 A1 | 9/2011 | Rivers et al. | |
| 2012/0191113 A1 | 7/2012 | Shturman | |
| 2013/0018398 A1 | 1/2013 | Rivers et al. | |
| 2013/0018399 A1 | 1/2013 | Rivers et al. | |
| 2013/0023913 A1 | 1/2013 | Rivers et al. | |
| 2013/0253552 A1 | 9/2013 | Schoenle et al. | |
| 2014/0005699 A1 | 1/2014 | Bonnette et al. | |

\* cited by examiner

DEVICES, SYSTEMS AND METHODS FOR AN OSCILLATING CROWN DRIVE FOR ROTATIONAL ATHERECTOMY

CROSS-REFERENCE TO RELATED APPLICATIONS

This application is a continuation-in-part of U.S. patent application Ser. No. 14/208,585, filed Mar. 13, 2014, which claims the benefit of U.S. Provisional Application No. 61/782,184, filed Mar. 14, 2013, the entirety of which applications are hereby incorporated by reference.

FIELD OF THE INVENTION

The present disclosure generally relates to devices and systems relating to rotational atherectomy. More specifically, an oscillating driver is connected to a drive shaft with an abrading head mounted thereon. The result provides a rotational working diameter for the rotating abrasive element that is larger than its resting diameter.

DESCRIPTION OF THE RELATED ART

A variety of techniques and instruments have been developed for use in the removal or repair of tissue in arteries and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Rotational atherectomy procedures have become a common technique for removing such stenotic material. Such procedures are used most frequently to initiate the opening of calcified lesions in coronary arteries. Most often the rotational atherectomy procedure is not used alone, but is followed by a balloon angioplasty procedure, which, in turn, is very frequently followed by placement of a stent to assist in maintaining patentcy of the opened artery. For non-calcified lesions, balloon angioplasty most often is used alone to open the artery, and stents often are placed to maintain patentcy of the opened artery. Studies have shown, however, that a significant percentage of patients who have undergone balloon angioplasty and had a stent placed in an artery experience stent restenosis—i.e., blockage of the stent which most frequently develops over a period of time as a result of excessive growth of scar tissue within the stent. In such situations an atherectomy procedure is the preferred procedure to remove the excessive scar tissue from the stent (balloon angioplasty being not very effective within the stent), thereby restoring the patentcy of the artery.

Several kinds of rotational atherectomy devices have been developed for attempting to remove stenotic material. In one type of device, such as that shown in U.S. Pat. No. 4,990,134 (Auth), a burr covered with an abrasive abrading material such as diamond particles is carried at the distal end of a flexible drive shaft. The burr is rotated at high speeds (typically, e.g., in the range of about 150,000-190,000 rpm) while it is advanced across the stenosis. As the burr is removing stenotic tissue, however, it blocks blood flow. Once the burr has been advanced across the stenosis, the artery will have been opened to a diameter equal to or only slightly larger than the maximum outer diameter of the burr. Frequently more than one size burr must be utilized to open an artery to the desired diameter.

U.S. Pat. No. 5,314,438 (Shturman) discloses another atherectomy device having a drive shaft with a section of the drive shaft having an enlarged diameter, at least a segment of this enlarged surface being covered with an abrasive material to define an abrasive segment of the drive shaft. When rotated at high speeds, the abrasive segment is capable of removing stenotic tissue from an artery. Though this atherectomy device possesses certain advantages over the Auth device due to its flexibility, it also is capable only of opening an artery to a diameter about equal to the diameter of the enlarged abrading surface of the drive shaft since the device is not eccentric in nature.

U.S. Pat. No. 6,494,890 (Shturman) discloses a known atherectomy device having a drive shaft with an enlarged eccentric section, wherein at least a segment of this enlarged section is covered with an abrasive material. When rotated at high speeds, the abrasive segment is capable of removing stenotic tissue from an artery. The device is capable of opening an artery to a diameter that is larger than the resting diameter of the enlarged eccentric section due, in part, to the orbital rotational motion during high speed operation. Since the enlarged eccentric section comprises drive shaft wires that are not bound together, the enlarged eccentric section of the drive shaft may flex during placement within the stenosis or during high speed operation. This flexion allows for a larger diameter opening during high speed operation, but may also provide less control than desired over the diameter of the artery actually abraded. In addition, some stenotic tissue may block the passageway so completely that the Shturman device cannot be placed therethrough. Since Shturman requires that the enlarged eccentric section of the drive shaft be placed within the stenotic tissue to achieve abrasion, it will be less effective in cases where the enlarged eccentric section is prevented from moving into the stenosis. The disclosure of U.S. Pat. No. 6,494,890 is hereby incorporated by reference in its entirety.

U.S. Pat. No. 5,681,336 (Clement) provides a known eccentric tissue removing burr with a coating of abrasive particles secured to a portion of its outer surface by a suitable binding material. This construction is limited, however because, as Clement explains at Col. 3, lines 53-55, that the asymmetrical burr is rotated at "lower speeds than are used with high speed ablation devices, to compensate for heat or imbalance." That is, given both the size and mass of the solid burr, it is infeasible to rotate the burr at the high speeds used during atherectomy procedures, i.e., 20,000-200,000 rpm. Essentially, the center of mass offset from the rotational axis of the drive shaft would result in development of significant centrifugal force, exerting too much pressure on the wall of the artery and creating too much heat and excessively large particles.

Thus, a need exists in the art generally for a rotational atherectomy device, system and method that allows for increasing the working diameter of an abrading head.

BRIEF SUMMARY OF THE INVENTION

An embodiment of a rotational atherectomy device includes a non-oscillating drive shaft, an oscillating section, an oscillating drive shaft, an abrading head, and a pulsator. The non-oscillating drive shaft includes a lumen therethrough and a rotational axis. The oscillating section includes a radially offsetting drive shaft attachment fixedly attached to the non-oscillating drive shaft proximate a distal end thereof. The drive shaft attachment includes a centered lumen in fluid communication with the lumen of the non-oscillating drive shaft and coincident with the rotational axis of the non-oscillating drive shaft. The drive shaft attachment further includes an attachment point radially offset from the centered lumen. The oscillating drive shaft is attached at its proximal end to the attachment point, and the abrading head is fixedly attached to the oscillating drive shaft proximate a distal end thereof. The pulsator is configured for introducing pulsations for dislodging at least a portion of an atheromatous material from a vasculature.

Another embodiment of a rotational atherectomy device includes a prime mover, a drive shaft, an abrading head, and a pulsator. The drive shaft is rotatably coupled, at its proximal end, to the prime mover and extends distally therefrom. The abrading head is fixedly attached to the drive shaft proximate a distal end thereof. The pulsator is configured for introducing pulsations for dislodging at least a portion of an atheromatous material from a vasculature.

DETAILED DESCRIPTION

Figure 1:
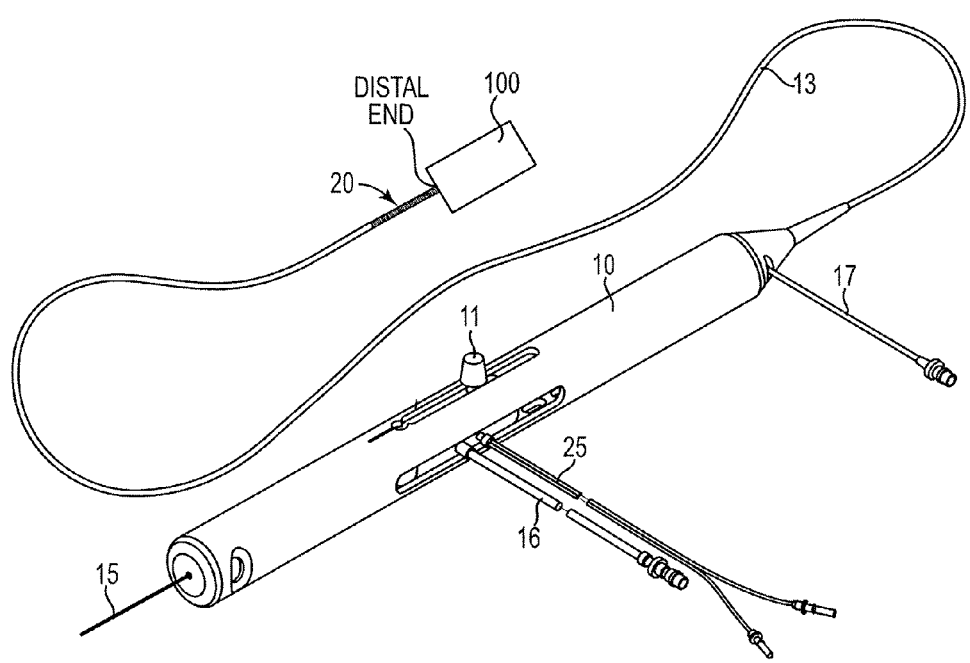
FIG. 1 illustrates a perspective view of one embodiment of the present invention.

While the disclosed embodiments are amenable to various modifications and alternative forms, specifics thereof are shown by way of example in the drawings and described in detail herein. It should be understood, however, that the intention is not to limit the disclosure to the particular embodiments described with reference to the appended figures. To the contrary, the intention is to cover all modifications, equivalents, and alternatives falling within the spirit and scope of the invention.

Various embodiments of the present invention may be incorporated into a rotational atherectomy system as described generally in U.S. Pat. No. 6,494,890, entitled "ECCENTRIC ROTATIONAL ATHERECTOMY DEVICE," which is incorporated herein by reference. Additionally, the disclosure of the following co-owned patents or patent applications are herein incorporated by reference in their entireties: U.S. Pat. No. 6,295,712, entitled "ROTATIONAL ATHERECTOMY DEVICE"; U.S. Pat. No. 6,132,444, entitled "ECCENTRIC DRIVE SHAFT FOR ATHERECTOMY DEVICE AND METHOD FOR MANUFACTURE"; U.S. Pat. No. 6,638,288, entitled "ECCENTRIC DRIVE SHAFT FOR ATHERECTOMY DEVICE AND METHOD FOR MANUFACTURE"; U.S. Pat. No. 5,314,438, entitled "ABRASIVE DRIVE SHAFT DEVICE FOR ROTATIONAL ATHERECTOMY"; U.S. Pat. No. 6,217,595, entitled "ROTATIONAL ATHERECTOMY DEVICE"; U.S. Pat. No. 5,554,163, entitled "ATHEREC- TOMY DEVICE"; U.S. Pat. No. 7,507,245, entitled "ROTATIONAL ANGIOPLASTY DEVICE WITH ABRASIVE CROWN"; U.S. Pat. No. 6,129,734, entitled "ROTATIONAL ATHERECTOMY DEVICE WITH RADIALLY EXPANDABLE PRIME MOVER COUPLING"; U.S. Pat. No. 8,597,313, entitled "ECCENTRIC ABRADING HEAD FOR HIGH-SPEED ROTATIONAL ATHERECTOMY DEVICES"; U.S. Pat. No. 8,439,937, entitled "SYSTEM, APPARATUS AND METHOD FOR OPENING AN OCCLUDED LESION"; U.S. Pat. Pub. No. 2009/0299392, entitled "ECCENTRIC ABRADING ELEMENT FOR HIGH-SPEED ROTATIONAL ATHERECTOMY DEVICES"; U.S. Pat. Pub. No. 2010/0198239, entitled "MULTI-MATERIAL ABRADING HEAD FOR ATHERECTOMY DEVICES HAVING LATERALLY DISPLACED CENTER OF MASS"; U.S. Pat. Pub. No. 2010/0036402, entitled "ROTATIONAL ATHERECTOMY DEVICE WITH PRE-CURVED DRIVE SHAFT"; U.S. Pat. Pub. No. 2009/0299391, entitled "ECCENTRIC ABRADING AND CUTTING HEAD FOR HIGH-SPEED ROTATIONAL ATHERECTOMY DEVICES"; U.S. Pat. Pub. No. 2010/0100110, entitled "ECCENTRIC ABRADING AND CUTTING HEAD FOR HIGH-SPEED ROTATIONAL ATHERECTOMY DEVICES"; U.S. Design Pat. No. D610258, entitled "ROTATIONAL ATHERECTOMY ABRASIVE CROWN"; U.S. Design Pat. No. D6107102, entitled "ROTATIONAL ATHERECTOMY ABRASIVE CROWN"; U.S. Pat. Pub. No. 2009/0306689, entitled "BIDIRECTIONAL EXPANDABLE HEAD FOR ROTATIONAL ATHERECTOMY DEVICE"; U.S. Pat. Pub. No. 2010/0211088, entitled "ROTATIONAL ATHERECTOMY SEGMENTED ABRADING HEAD AND METHOD TO IMPROVE ABRADING EFFICIENCY"; U.S. Pat. Pub. No. 2013/0018398, entitled "ROTATIONAL ATHERECTOMY DEVICE WITH ELECTRIC MOTOR"; and U.S. Pat. No. 7,666,202, entitled "ORBITAL ATHERECTOMY DEVICE GUIDE WIRE DESIGN." It is contemplated by this invention that the features of one or more of the embodiments of the present invention may be combined with one or more features of the embodiments of atherectomy devices described therein.

FIG. 1 illustrates one embodiment of a rotational atherectomy device according to the present invention. The device includes a handle portion 10; an elongated, flexible non-oscillating and therefore fixed axis drive shaft 20 with a lumen therethrough for passage of a guidewire and further having an oscillating section 100 attached thereto proximate to the distal end of the drive shaft 20 and comprising a radially offsetting driveshaft attachment 102 and abrading head 106 mounted or otherwise disposed on a flexible oscillating drive shaft 110. Oscillating section 100 and its components and functionality will be discussed in further detail below. Elongated catheter 13 is also illustrated as extending distally from the handle portion 10. The non-oscillating fixed axis drive shaft 20 is constructed from helically coiled wire as is known in the art and has an outer surface 24 and an inner surface 22 defining an inner lumen, permitting the non-oscillating drive shaft 20 to be advanced and rotated over a guide wire. The catheter 13 has a lumen in which most of the length of the drive shaft 20 is disposed, except for the oscillating section 100. A fluid supply line 17 may be provided for introducing a cooling and lubricating solution (typically saline or another biocompatible fluid) into the catheter 13.

The handle 10 desirably contains a turbine (or similar rotational drive mechanism) for rotating the drive shaft 20 at high speeds. The handle 10 typically may be connected to a power source, such as compressed air delivered through a tube 16. A pair of fiber optic cables 25, alternatively a single fiber optic cable may be used, may also be provided for monitoring the speed of rotation of the turbine and drive shaft 20 (details regarding such handles and associated instrumentation are well known in the industry. The handle 10 also desirably includes a control knob 11 for advancing and retracting the turbine and drive shaft 20 and attached oscillating section 100 with respect to the catheter 13 and the body of the handle.

Figure 2:
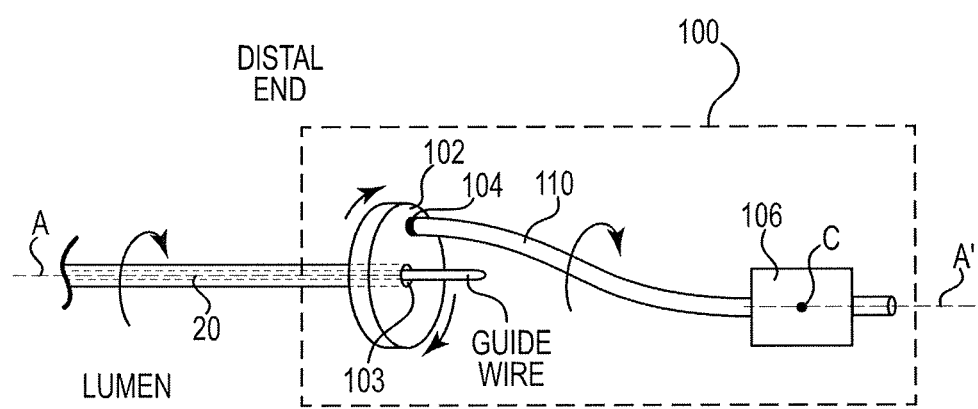
FIG. 2 illustrates a partial cutaway and side view of one embodiment of the present invention.

Turning now to FIG. 2, the oscillating section 100 is attached proximate to the distal end of the non-oscillating drive shaft 20 and comprises the radially offsetting drive-shaft attachment 102 and abrading head 106 mounted or otherwise disposed on a flexible oscillating drive shaft 110.

The radially offsetting drive shaft attachment 102 comprises, as illustrated, a circular structure with a centered lumen 103 therethrough which is coincident and in fluid communication with the non-oscillating drive shaft 20 lumen. In this configuration, as the non-oscillating drive shaft 20 rotates, the radially offsetting drive shaft attachment 102 will spin concentrically with the drive shaft 20 because the center of mass of the circular drive shaft attachment 102 is also coincident with the rotational axis A of the non-oscillating drive shaft 20. FIG. 2 illustrates that the guidewire may pass through non-oscillating drive shaft 20 lumen as well as through centered lumen 103. The skilled artisan will recognize that the circular form of the illustrated embodiment of drive shaft attachment 102 is but one of several forms that are functionally possible. What is required is that the center of mass of the drive shaft attachment 102 is located in the center of the centered lumen 103.

The flexible oscillating drive shaft 110 is attached to the radially offsetting drive shaft attachment 102 at an attachment point 104 radially offset from the centered lumen 103. The distance of this radial offset, together with the rotational speed of the drive shaft 20, and therefore oscillating section 100, and the mass, and location thereof, of the abrading head 106 determine the working diameter of the abrading head 106 during operation. An increase in working diameter of the abrading head 106 is directly related to greater distance between attachment point 104 and centered lumen 103, increasing rotational speed of drive shaft 20 and oscillating section 100, and increased mass and radially offsetting of the increased mass of abrading head 106. Further, as discussed below, the location of the radially offset center of mass C and the attachment point 104 relative to each other in a longitudinal plane also has a direct effect on the flexing of oscillating drive shaft 110 and, therefore, the magnitude of the working diameter achieved by the abrading head 106 during rotational operation.

Figure 3:
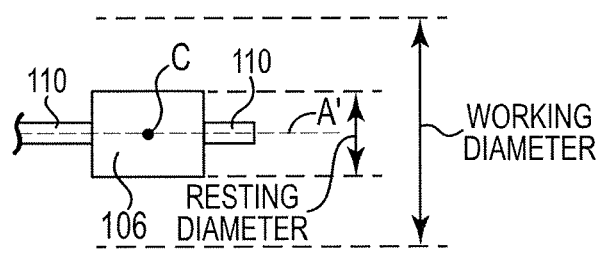
FIG. 3 illustrates a partial cutaway and side view of one embodiment of the present invention.

The abrading head 106 is illustrated in FIGS. 2 and 3 as a concentric, i.e., longitudinally and laterally or radially symmetrical construction about the oscillating drive shaft 110 to which it is attached by means well understood in the art. As a result, the center of mass C of abrading head 106 is, in FIGS. 2 and 3, coincident with the rotational axis A' of oscillating drive shaft 110.

Figure 4:
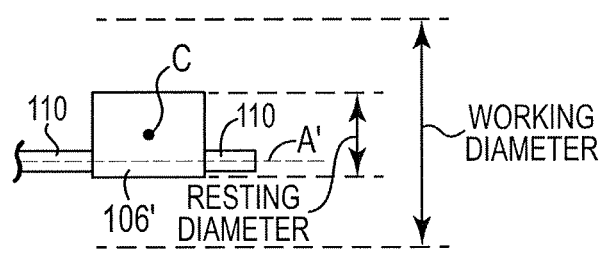
FIG. 4 illustrates a partial cutaway and side view of one embodiment of the present invention.

Alternatively, as shown in FIG. 4, abrading head 106 may comprise a center of mass C that is radially offset from the rotational axis A' of oscillating drive shaft 110. The skilled artisan will recognize that the center of mass C may be moved radially away with respect to the rotational axis A' of oscillating drive shaft 110 by creating a purely geometric eccentricity as illustrated in FIG. 4 having at least a radial or lateral geometric asymmetry or by using materials of differing density in either a geometrically concentric or eccentric abrading head 106.

Figure 5:
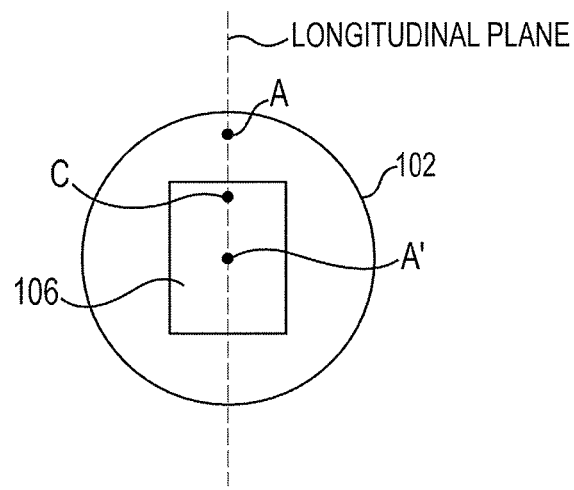
FIG. 5 illustrates an end view of one embodiment of the present invention.

In both cases, as shown, the working diameter achieved by abrading head 106 is greater than its resting diameter. A damping effect may be added to the oscillating section 100 using the technique illustrated in FIG. 4 by aligning the radially offset center of mass C of abrading head 106 with the attachment point 104 of radially offsetting drive shaft attachment 102 so that there is a 0-degree offset between attachment point 104 and radially offset center of mass C in the longitudinal plane as in FIG. 5.

Figure 6:
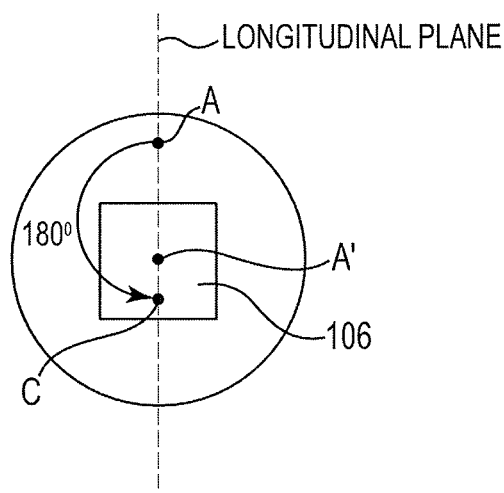
FIG. 6 illustrates an end view of one embodiment of the present invention.

Alternatively, as in FIG. 6 the flexing of oscillating drive shaft 110 may be enhanced by shifting the radially offset center of mass C of abrading head 106 180-degrees so that the radially offset center of mass is located on the opposite side of oscillating drive shaft's axis of rotation A' as compared with attachment point 104.

In all cases, whether abrading head 106 is concentric or eccentric, the working diameter achieved during high speed rotation is greater than the working diameter of abrading head 106.

In some embodiments, the high speed rotation of the abrading head 106 must be sustained for an extended period of time in order to achieve the desired results. However, sustained high speed rotation of the components introduced into the blood stream can cause hemolysis. Also, high speed rotation of the components can generate heat in the rotating components and in items, including body parts, that contact the rotating components. If the generated heat is not mitigated or limited, thermal damage can ensue. In certain embodiments, saline is used as a heat transfer fluid and/or as a lubricant for minimizing the heat generation. Additionally, in certain applications, sanding cannot be used for removing excessive calcium deposits, for example in the vessel, intima, adventitia, etc., without also damaging or removing healthy tissue.

As an alternative, or in addition, to operating the abrading head 106 at high rotational speeds, certain embodiments of the rotational atherectomy device include a pulsator for dislodging or breaking at least a portion of the atheromatous material in the vicinity of the abrading head 106. The pulsator, in certain embodiments, is configured for introducing pulsation or vibrations to the treatment site at a plurality of intensities, or a plurality of frequencies, or both. In some embodiments, the pulsations can be applied as a discrete or a continuously variable force between a maximum and a minimum value. In certain embodiments, the pulsations can be applied as a burst of discrete or as a continuous force for a specified duration of time. In some embodiments, the intensity of the applied pulsations, i.e. the applied force, can be fixed or varied. In addition, or in the alternative, the frequency of applying the force can be fixed or varied.

In some embodiments, in addition to rotating the abrading head 106, the pulsator introduces pulsations to the treatment site. As such, by introducing high impact, low duration, and non-sustained pulsations, i.e., vibrations, during treatment, the atherectomy device can be tuned to provide appropriate shear rate of the cutting surface while delivering equivalent orbits as a device without a pulsator operating at sustained high rotational speeds. In certain embodiments, with the introduction of pulsations in addition to and while rotating the abrading head 106, the overall rotational speed and the average rotational speed can be reduced while maintaining or delivering substantially similar effective treatment as that provided at sustained high rotational speeds without pulsations. And, with the reduction in the rotational speeds, hemolysis and thermal impact will be reduced or eliminated.

The pulsations, in some embodiments, can be introduced to one or more of the non-oscillating drive shaft 20, the oscillating drive shaft 110, and the abrading head 106 while rotating or while stationary. In certain embodiments, the prime mover, which is rotatably coupled with at least the non-oscillating drive shaft 20, can be operated in a manner by which pulsations (or vibrations) are introduced to one or both of the non-oscillating drive shaft 20 and the oscillating drive shaft 110. In a non-limiting exemplary embodiment, a coupling used for removably engaging the prime mover and the non-oscillating drive shaft 20 with one another can be configured for introducing pulsations into the non-oscillating drive shaft 20 which, in turn, will at least partially introduce pulsations into the oscillating drive shaft 110. For instance, in embodiments where one or more gears are used for rotatably coupling the prime mover and the non-oscillating drive shaft 20, the coupling can include at least one of the one or more gears having an irregular circumference. In some embodiments, the pulsations can be introduced by operating the prime mover at discrete or variable rotational speeds. For example, the rotation of an electric motor shaft can be disrupted by using a pulse width modulation motor controller. In certain embodiments, the rotation of the electric motor shaft can be disrupted by modulating the peak and/or the running current supplied to the motor. In certain embodiments wherein a turbine is used as the prime mover, the pulsator can be configured to discretely or continuously modulate one or both of a pressure and a flow rate of compressed fluid supplied to a turbine. The described embodiments are exemplary and should not be construed as limiting. Additional or alternative embodiments as my become apparent to one having ordinary skill in the art are considered as being within the metes and bounds of the instant disclosure.

In addition, or in the alternative, the pulsator can be configured for introducing pulsations into the one or both of the non-oscillating drive shaft 20 and the oscillating drive shaft 110. Furthermore, the pulsator can be also configured for introducing pulsations into the abrading head 106 while it is rotating or stationary at the treatment site. In a non-limiting exemplary embodiment, pulsations such as secondary inductive impulses are introduced into one or more of the drive shafts 20 and 110 and the abrading head 106. For instance, the pulsator can be configured as an ultrasonic device, a piezo-vibrator, electromechanical litoplasty, etc. These examples should not be construed as limiting. Additional or alternative embodiments as my become apparent to one having ordinary skill in the art are considered as being within the metes and bounds of the instant disclosure.

Referring back to FIG. 1, alternate embodiments of the rotational atherectomy device do not include the oscillation section 100, and the abrading head 106 is instead coupled to an elongated flexible drive shaft proximate a distal end thereof. In such embodiments, the device includes a handle substantially similar to the handle portion 10, and a prime mover disposed within the handle and rotatably coupled with the drive shaft proximate a proximal end thereof. Non-limiting exemplary embodiments of the device further include the pulsator configured for introducing pulsations substantially similar to and in substantially the same manner as described in the foregoing. Therefore, in the interest of brevity, details pertaining to the pulsator and the introduction of pulsations are not repeated. However, this should not be construed as limiting. Instead, all alternatives, enhancements, and modifications as may become apparent to a one having ordinary skill in the art are considered as being within the metes and bounds of the instant disclosure.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A rotational atherectomy device, comprising:
    a prime mover;
    a non-oscillating drive shaft having a lumen therethrough, a rotational axis and a distal end;
    an oscillating section attached proximate the distal end of the non-oscillating drive shaft, the oscillating section comprising:
        a radially offsetting drive shaft attachment fixedly attached to the non-oscillating drive shaft, the drive shaft attachment comprising:
            a centered lumen in fluid communication with the lumen of the non-oscillating drive shaft and coincident with the rotational axis of the non-oscillating drive shaft; and
            an attachment point radially offset from the centered lumen;
        an oscillating drive shaft comprising a proximal end attached to the attachment point; and
        an abrading head fixedly attached to the oscillating drive shaft proximate a distal end thereof, the prime mover adapted to rotate the non-oscillating drive shaft, the oscillating section and the abrading head; and
    a pulsator configured to introduce pulsations during the rotation of the abrading head for dislodging at least a portion of an atheromatous material from a vasculature.

2. The device of claim 1, wherein the pulsations comprise one or both of a plurality of intensities and a plurality of frequencies.

3. The device of claim 2, wherein the prime mover is rotatably coupled to the non-oscillating drive shaft proximate a proximal end thereof, wherein the pulsator operates the prime mover at a plurality of discrete rotational speeds.

4. The device of claim 3, wherein:
    the prime mover comprises an electric motor; and
    the pulsator comprises a pulse width modulator for modulating one or both of a peak current supplied to the prime mover and a running current through the prime mover.

5. The device of claim 3, wherein the prime mover comprises a turbine, and the pulsator modulates one or both of a pressure and a flow rate of a compressed fluid used for operating the prime mover.

6. The device of claim 2, wherein the pulsator comprises two or more gears configured for rotatably coupling the prime mover and the non-oscillating drive shaft.

7. The device of claim 6, wherein a rotational speed of the prime mover is different from a rotational speed of the non-oscillating drive shaft.

8. The device of claim 6, wherein at least one of the two or more gears comprises an irregular circumference.

9. The device of claim 2, wherein the pulsator comprises an inductor.

10. The device of claim 9, wherein the inductor is selected from the group consisting of an ultra-sonic generator and a piezo-vibrator.

11. The device of claim 2, wherein the pulsator generates one or more of energy waves, sound waves, and pressure waves.

12. The device of claim 2, wherein at least a portion of the pulsator is disposed on one or more of the non-oscillating drive shaft, the oscillating drive shaft, and at least a portion of the abrading head.

13. The device of claim 1, comprising a guide wire extending through the lumen of the non-oscillating drive shaft, wherein a displacement of the non-oscillating drive shaft over the guide wire induces a displacement of the oscillating section.

14. The device of claim 1, wherein the radially offsetting drive shaft attachment is circular.

15. The device of claim 1, wherein an operating diameter of the abrading head is greater than a resting diameter thereof.

16. The device of claim 1, wherein the abrading head is concentric to a rotational axis of the oscillating drive shaft.

17. The device of claim 16, wherein a center of mass of the abrading head coincides with a rotational axis of the oscillating drive shaft.

18. The device of claim 1, wherein the abrading head comprises materials of differing densities.

19. The device of claim 1, wherein at least a portion of the pulsator is disposed on at least a portion of the abrading head.

* * * * *